(12) United States Patent
Chamney et al.

(10) Patent No.: US 11,896,747 B2
(45) Date of Patent: *Feb. 13, 2024

(54) PRESCRIPTION COMPATIBILITY CHECKING FOR A MEDICAL DEVICE

(71) Applicants: Fresenius Medical Care Holdings, Inc., Waltham, MA (US); Fresenius Medical Care Deutschland GmbH, Bad Homburg (DE)

(72) Inventors: Paul Chamney, Hertfordshire (GB); Harvey Cohen, Newton, MA (US)

(73) Assignees: Fresenius Medical Care Holdings, Inc., Waltham, MA (US); Fresenius Medical Care Deutschland GmbH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,966

(22) Filed: Jul. 1, 2022

(65) Prior Publication Data

US 2022/0331499 A1    Oct. 20, 2022

Related U.S. Application Data

(62) Division of application No. 15/650,320, filed on Jul. 14, 2017, now Pat. No. 11,389,575.

(51) Int. Cl.
*A61M 1/28*    (2006.01)
*A61M 1/14*    (2006.01)
(Continued)

(52) U.S. Cl.
CPC .............. *A61M 1/14* (2013.01); *A61M 1/152* (2022.05); *A61M 1/159* (2022.05);
(Continued)

(58) Field of Classification Search
CPC .............................. G06F 3/0488; A61M 1/28
See application file for complete search history.

(56) References Cited

U.S. PATENT DOCUMENTS

| 7,981,281 B2 | 7/2011 | Yu et al. |
| 8,529,496 B2 | 9/2013 | Britton et al. |
| (Continued) | | |

FOREIGN PATENT DOCUMENTS

| AU | 2003237178 | 11/2003 |
| CA | 2125300 | 11/1995 |
| (Continued) | | |

OTHER PUBLICATIONS

U.S. Appl. No. 15/497,529, filed Apr. 26, 2017, 44 pages.
(Continued)

*Primary Examiner* — Reginald R Reyes
(74) *Attorney, Agent, or Firm* — Fish & Richardson P.C.

(57) ABSTRACT

A medical treatment machine, such as a home dialysis machine, can receive prescription parameters that define parameters of a medical treatment to be administered to a patient. A medical prescription is entered by a clinician into a clinical information system (CIS) that calls a system to evaluate the compatibility of the entered prescription by transmitting the prescription parameters to a server that has access to a database of medical devices and their operational parameters. The server compares the treatment parameters of the medical prescription to the operational parameters of the medical device and generates a prescription compatibility response indicting if the treatment parameters of the medical prescription can be executed by the medical device. The server returns to the CIS the prescription compatibility response to allow the prescription, e.g. in a digital or program form, to be securely transmitted or delivered via a connected health system to the medical device.

21 Claims, 9 Drawing Sheets

(51) Int. Cl.
    *G16H 20/40*     (2018.01)
    *G16H 40/67*     (2018.01)
    *G16H 10/60*     (2018.01)
    *G06F 3/0488*     (2022.01)
    *A61M 1/34*     (2006.01)
    *A61M 1/16*     (2006.01)

(52) U.S. Cl.
    CPC ........... *G06F 3/0488* (2013.01); *G16H 10/60* (2018.01); *G16H 20/40* (2018.01); *G16H 40/67* (2018.01); *A61M 1/16* (2013.01); *A61M 1/28* (2013.01); *A61M 1/34* (2013.01); *A61M 2205/3553* (2013.01); *A61M 2205/3584* (2013.01); *A61M 2205/52* (2013.01); *A61M 2205/6009* (2013.01)

(56) References Cited

U.S. PATENT DOCUMENTS

| | | | |
|---|---|---|---|
| 8,954,190 B2 * | 2/2015 | Braunstein | G07F 9/001 |
| | | | 700/242 |
| 9,050,411 B2 | 6/2015 | Kelly et al. | |
| 9,178,891 B2 | 11/2015 | Wang et al. | |
| 9,251,310 B2 | 2/2016 | McNally et al. | |
| 9,514,283 B2 | 12/2016 | Childers et al. | |
| 9,582,645 B2 | 2/2017 | Yu et al. | |
| 9,675,745 B2 | 6/2017 | Kelly et al. | |
| 9,690,905 B2 | 7/2017 | Yu et al. | |
| 9,697,334 B2 | 7/2017 | Yu et al. | |
| 9,800,663 B2 | 10/2017 | Arrizza | |
| 9,861,733 B2 | 1/2018 | Burbank et al. | |
| 2002/0052760 A1 | 5/2002 | Munoz et al. | |
| 2009/0037216 A1 | 2/2009 | Bluemler et al. | |
| 2010/0138534 A1 | 6/2010 | Mutnuru et al. | |
| 2011/0082708 A1 | 4/2011 | Pourfallah | |
| 2013/0172806 A1 | 7/2013 | Griessmann et al. | |
| 2013/0193041 A1 | 8/2013 | Rohde | |
| 2013/0201222 A1 | 8/2013 | Doyle et al. | |
| 2013/0204098 A1 * | 8/2013 | Chamney | A61G 15/02 |
| | | | 600/301 |
| 2014/0276375 A1 * | 9/2014 | Minkus | A61M 1/1657 |
| | | | 705/2 |
| 2015/0149212 A1 | 5/2015 | Rolia et al. | |
| 2015/0370973 A1 | 12/2015 | Jones | |
| 2016/0082172 A1 * | 3/2016 | Miller | A61M 1/1605 |
| | | | 210/85 |
| 2016/0206800 A1 | 7/2016 | Tanenbaum et al. | |
| 2016/0239637 A1 | 8/2016 | Miller et al. | |
| 2016/0261974 A1 | 9/2016 | Arrizza | |
| 2016/0361500 A1 | 12/2016 | Iwasaki | |
| 2017/0076069 A1 | 3/2017 | Moissl et al. | |
| 2017/0087290 A1 | 3/2017 | Medina et al. | |
| 2018/0316505 A1 * | 11/2018 | Cohen | A61M 1/282 |
| 2019/0018931 A1 * | 1/2019 | Chamney | A61M 1/152 |
| 2020/0259664 A1 * | 8/2020 | Cohen | H04L 9/3247 |

FOREIGN PATENT DOCUMENTS

| | | |
|---|---|---|
| CN | 1426565 | 6/2003 |
| CN | 1856793 | 11/2006 |
| CN | 103415852 | 11/2013 |
| CN | 104254857 | 12/2014 |
| CN | 104520856 | 4/2015 |
| CN | 105102012 | 11/2015 |
| EP | 2618864 | 7/2013 |
| GB | 201322331 | 1/2014 |
| JP | 2002-297778 | 10/2002 |
| JP | 2012-254251 | 12/2012 |
| JP | 2015-519133 | 7/2015 |
| JP | 2016-512463 | 4/2016 |
| JP | 2018-528806 | 10/2018 |
| WO | WO 2002/029664 | 4/2002 |
| WO | WO 2006/128536 | 12/2006 |
| WO | WO 2012/118639 | 9/2012 |
| WO | WO 2014/159918 | 10/2014 |
| WO | WO 2015/156134 | 10/2015 |
| WO | WO 2016/196023 | 12/2016 |
| WO | WO 2017/030976 | 2/2017 |

OTHER PUBLICATIONS

International Search Report and Written Opinion in International Application No. PCT/US2018/041437, dated Oct. 16, 2018, 14 pages.

International Preliminary Report on Patentability in Application No. PCT/US2018/041437, dated Jan. 14, 2020, 8 pages.

Anonymous, "EAN system: Applications in the healthcare industry," Enterprise Standardization, May 15, 2002, 37-38, 6 pages (with machine translation).

* cited by examiner

710

Receiving patient data from a CIS, including a patient ID and a medical prescription with treatment parameters for use in conducting a medical procedure on the patient with a patient's in-home medical device

720

Accessing a database of operational parameters for a plurality of medical devices, including the patient's medical device

730

Comparing the treatment parameters of the patient's prescription to the operational parameters of the patient's medical device from the database

740

Based on the comparison, generating a prescription compatibility response that indicates if the treatment parameters of the prescription are able to be executed by the patient's medical device

750

Providing the prescription compatibility response to the CIS

FIG. 7

PRESCRIPTION COMPATIBILITY CHECKING FOR A MEDICAL DEVICE

CROSS-REFERENCE TO RELATED APPLICATIONS

This application is a divisional application of and claims the benefit of priority under 35 U.S.C. 121 to U.S. application Ser. No. 15/650,320, filed on Jul. 14, 2017, the contents of which are hereby incorporated by reference.

TECHNICAL FIELD

This disclosure relates to distributing medical prescriptions and confirming the prescription's compatibility with a medical device configured to administer the medical prescription.

BACKGROUND

Medical treatment machines can be designed to aid in the diagnosis, monitoring, and/or treatment of a variety of medical conditions. One example of a medical treatment machine is a dialysis machine. Dialysis is a treatment used to support a patient with insufficient renal function. The two principal dialysis methods are hemodialysis and peritoneal dialysis. During hemodialysis ("HD"), the patient's blood is passed through a dialyzer of the dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD ("CCPD"). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

An example of the present disclosure is a method of determining compatibility between a medical prescription and a remote home medical device. The method includes receiving, using a computer processor of a server, patient data from a clinical information system via the Internet. The patient data includes an identification of a patient, and prescription parameters including treatment parameters for use in conducting a medical procedure according to a medical prescription on a patient using the home medical device. The method includes accessing, using the computer processor of the server, a database containing operational parameters of a plurality of medical devices, including operational parameters of the home medical device, performing a compatibility check, using the computer processor of the server, of the prescription parameters of the patient's medical prescription to the operational parameters of the patient's home medical device from the database. The method includes generating, using the computer processor of the server, based on the compatibility check, a prescription compatibility response indicting if the prescription parameters of the medical prescription are able to be executed by the patient's home medical device in order to conduct the medical procedure, and providing, using the computer processor of the server, the prescription compatibility response via the Internet to the clinical information system.

In some examples, the medical device is a peritoneal dialysis machine. In some examples, the medical device is a hemodialysis machine.

In some examples, the patient data includes patient treatment limitations. In some examples, generating the prescription compatibility response includes determining if the prescription parameters of the medical prescription are able to be executed by the patient's home medical device in order to conduct the medical procedure within the patient treatment limitations.

In some examples, where the patient data includes an identification of the patient's home medical device for use in conducting the medical procedure. In some examples, the database containing operational parameters of the plurality of medical devices, includes the operational parameters of the patient's home medical device identified in the received patient data. In some examples, the database containing operational parameters of the plurality of medical devices, includes a plurality of identifications of medical devices associated with a corresponding plurality of patients including an identification of a medical device associated with the received patient information, the method further includes confirming, using the computer processor of the server, based on the received patient identification, the identification of the patient's medical device at the patient's home based on the identification of the medical device associated with the received patient information in the database.

In some examples, generating the prescription compatibility response based on the comparing is further based on the confirming. In some examples, the patient data includes patient treatment limitations, and the method further includes calculating, using the computer processor of the server, a simulated outcome of the medical procedure based on the received patient medical prescription and the operational parameters of the patient medical device, and the generating the prescription compatibility response includes determining if the simulated outcome of the medical procedure satisfies one or more of: the medical prescription, the patient treatment limitations, and the operational parameters of the medical device.

In some examples, prescription compatibility response indicates if the received medical prescription is comparable or not compatible with the patient and if the received medical prescription is comparable or not compatible with patient's medical device.

In some examples, the method includes accepting, using the computer processor of the server, the received patient prescription based on the prescription compatibility response.

In some examples, the method includes sending, using the computer processor of the server, the accepted medical prescription via the Internet to the medical device in the patient's home for use in conducting the medical procedure according to the accepted medical prescription.

In some examples, the method includes sending, using the computer processor of the server, the accepted medical prescription via the Internet to a patient's email address for use in conducting the medical procedure according to the accepted medical prescription.

In some examples, the method includes denying, using the computer processor of the server, the received patient prescription based on prescription compatibility response.

In some examples, the method includes sending, using the computer processor of the server, information regarding the denied medical prescription via the Internet to the clinical information system.

In some examples, the method includes providing, using the computer processor of the server, a prescription compatibility feedback via the Internet to the clinical information system, the prescription compatibility feedback including results of the comparing.

In some examples, the method includes providing, using the computer processor of the server, and based on the prescription compatibility response, a signal via the Internet to the clinical information system for use in enabling a user of a terminal of the clinical information system to download the received medical prescription onto a removable physical storage device interfaced with the terminal, the removable physical storage device being configured to transfer the medical prescription to the medical device in the patient's home for use in conducting the medical procedure.

In some examples, performing the compatibility check further includes performing a calculation on the treatment parameters to a determine a least one characteristic of the medical treatment and comparing a result of the calculation to the operational parameters of the medical device from the database.

In some examples, the operation parameters of the medical devices in the database includes capacity limits and wherein the at least one characteristic identified from the calculation on the treatment parameters includes determining a total fluid delivery of the medical treatment, and wherein comparing the treatment parameters of the medical prescription to the operational parameters of the medical apparatus further includes comparing the total fluid delivery to the capacity limits of the medical device from the database.

In some examples, the clinical information system includes a healthcare computer network, independent from the server system, including at least one server configured to maintain and store patient health records, and a plurality of user terminals configured to provide point-of-care access to the patient health records by medical professionals.

Another example of the present disclosure is connected health system including a cloud-based application that facilitates data transfer between components of the system via the Internet, a remote medical device, wherein the medical device is configured to receive data from the cloud-based application, a database containing operational parameters of a plurality of medical devices, including the operational parameters of the remote medical device, a clinical information system configured to receive prescription parameters from a clinician, and a computer server. The computer server includes a processor configured to (i) receive, from a clinical information system, a digital prescription file comprising prescription parameters for use in conducting a medical procedure on a patient using the remote medical device, (ii) identify operational parameters of the remote medical device from the database, (iii) perform a compatibility check of the prescription parameters of the digital prescription file to the operational parameters of the remote medical device, (iv) generate, based on the compatibility check, a prescription compatibility response indicting if the prescription parameters are able to be executed by the remote medical device in order to conduct the medical procedure, (v) provide the prescription compatibility response to the clinical information system, (iv) transmit the digital prescription file to the remote medical device.

Other aspects, features, and advantages of the subject matter included herein will be apparent from the description and drawings, and from the claims.

DESCRIPTION OF DRAWINGS

FIG. 7 illustrates a system for checking the compatibility of a digital prescription file with a patient's home medical device.

Like reference symbols in the various drawings indicate like elements.

DETAILED DESCRIPTION

Figure 1:
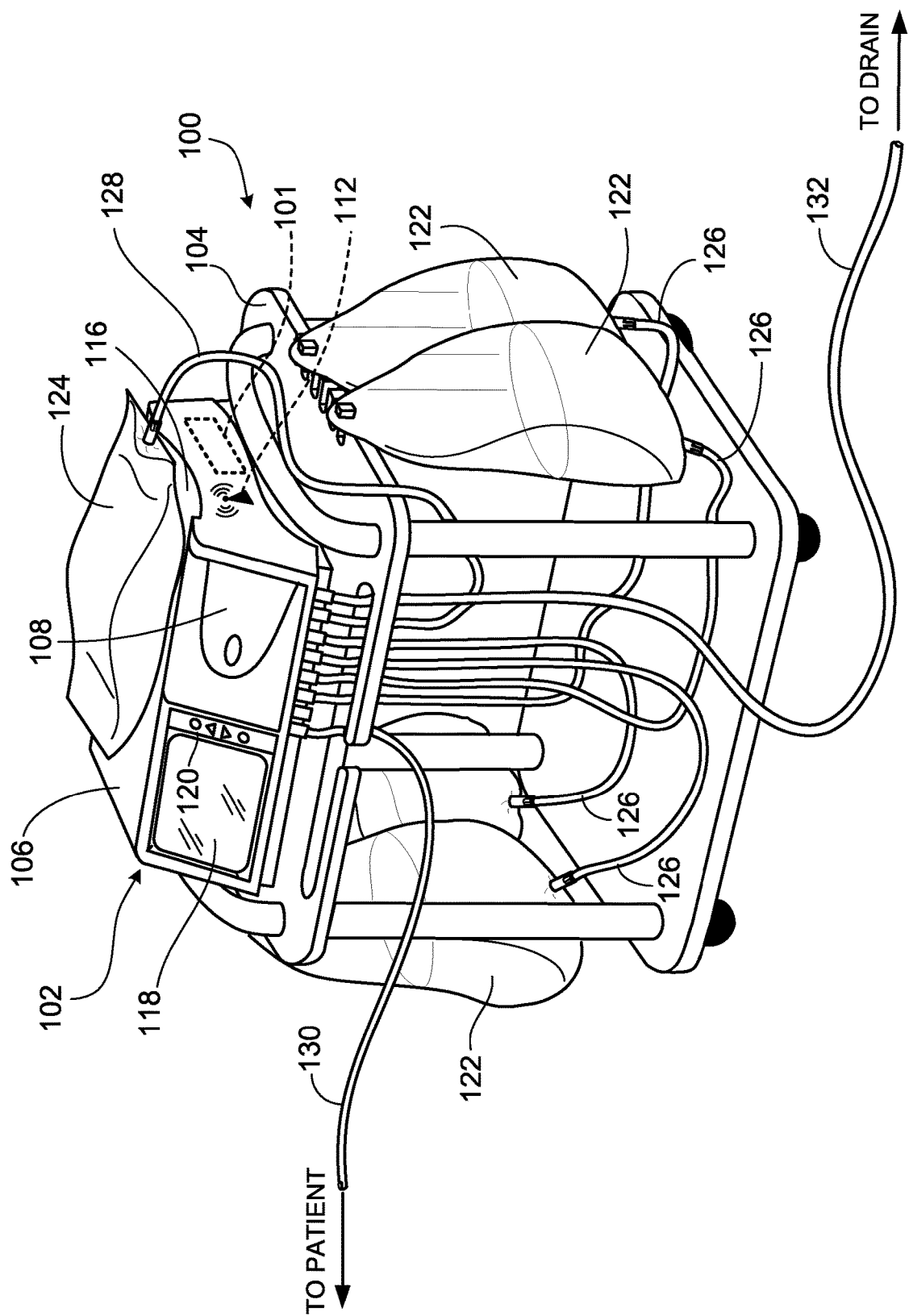
FIG. 1 is a front perspective view of a peritoneal dialysis machine connected to a network.

Described herein is a system and included techniques for checking compatibility of a medical prescription to the operational capabilities of a remote medical device (e.g. a home dialysis machine) of a patient. The system described herein facilitates entry by a clinician or doctor of a medical prescription into a clinical information system (CIS), which is a system in the clinical setting that stores the electronic health records (EHR) used a clinician, doctor, clinic and/or hospital to manage treatment of a patient, and enables the CIS to provide the digital prescription parameters to a remote server and/or service of a connected health system (CHS). The remote server and/or service provides a confirmation to the CIS that the digital prescription is compatible with a patient's medical device for conducting the treatment specified in the prescription. The term "Unity" may be used herein to refer generally to an implementation of the remote server and/or service capabilities for the prescription compatibility checking system described herein. The technique also enables the CIS, once the prescription has been indicated as compatible, to download the digital prescription onto a removable storage device to physically deliver the digital prescription to the patient's medical device or, alternatively, to instruct the CHS server conducting the compatibility check to send the prescription directly to the patient's medical device via a network or Internet-based transmission.

In some implementations, the term "digital prescription file" may be understood to include and refer to a set of programming instructions that may be used to carry out a medical treatment that has been medically prescribed by an appropriate doctor or other medical practitioner. In some implementations, the term "prescription" may be understood to refer to the medical treatment that the doctor actually prescribes to the patient and may be represented as prescription parameters in the patient's electronic health record (EHR). This prescription (e.g. prescription parameters) may be appropriately translated, formatted, encrypted and/or otherwise converted into the digital prescription file that contains the program and/or instruction sets for the medical device (e.g., the dialysis machine) to carry out the prescribed medical treatment.

Within the clinical setting, workflow integration into existing clinical systems has significant value through reducing the work steps to be performed by both the clinician and physician (reduction in multiple entry of information). To facilitate an efficient workflow when managing prescriptions intended for, for example, home dialysis machines (HDM), examples of the present disclosure describe processes to allow a clinic to create and manage the HDM prescription within their own clinical information system (CIS). In one example, this is accomplished by leveraging a web based compatibility check service that allows the clinician to know the entered prescription is safe and compatible with the intended HDM and patient. The clinician enters the prescription, according to a provided specification, into their clinical information system (CIS). Upon entry, the CIS will call a prescription compatibility service, which passes the required attributes for the compatibility service to make the determination if the prescription entered will pass the checks. Subsequently, the service returns a pass/fail response with the feedback to guide the clinician to next steps. If the prescription passed the compatibility check, then the clinician is free to save the prescription in the CIS for delivery to the patient's HDM. If the prescription fails, the compatibility check then the clinician is provided feedback on the failures so the clinician may make further adjustments to the prescription to bring it within compatibility limits.

In order to bring this approach into practical context, some example implications and user experience are as follows:

In some instances, generation of the prescription is entirely the clinician's responsibility. The prescription entered by the clinician may be transmitted as prescription parameters from the user interface, through an API, to the Unity system and thereafter securely, as a digital prescription file, through the Connected Health System to the target HDM. The API makes no changes to the prescription parameters.

In some instances, examples the systems and techniques described herein make no assessment of the clinical efficacy of the prescription.

In some instances, examples the systems and techniques described herein shall check the prescription for compatibility with the target HDM. This means that the prescription shall be checked to ensure that it can be performed within the bounds of the target HDM. As an example, if the clinician requests in the prescription that the patient be treated with a volume of fluid which exceeds the capacity of the target HDM can deliver, the prescription would not be compatible with the target HDM.

In some instances, examples the systems and techniques described herein perform calculations on the data that has been entered in the prescription in order to determine if any target machine bounds have been exceeded.

In some instances, a patient parameter check is combined with the prescription compatibility checks. In this event, the following workflow applies: A user enters patient parameter information via a reference system user interface in the CIS and the CIS makes a request to the server to perform a compatibility check. The server interfaces the CHS to verify that the service provider is an authorized user of the clinic's terminal and CHS. Subsequently, the CIS makes a request to perform a compatibility check. Patient parameter data is sent through an application program interface (API) to a compatibility check service application running on the remote server. In some instances, this check is specific to a given HDM. A notification is returned if the patient parameter data passes the patient parameter check. The patient parameter data may be saved to the patient's EHR within the CIS. If the patient parameter compatibility check fails an error status is returned. When sending a patient parameter data to the CHS cloud (that may be also referred to herein as Reciprocity) or the flash drive, it shall be included in the header of the prescription parameter file. As further discussed elsewhere herein, Reciprocity may generate a digital prescription file by appropriately processing and encrypting the prescription parameter file for purposes of facilitating secure transmission of the prescription to the home medical device.

In another embodiment, if the compatibility check passes, the confirmation be returned to the clinician that may include a summary of the prescription parameters that have been entered through the user interface If the compatibility check fails, an error message is returned to the clinician indicating the likely cause and which limits have been exceeded. As an example, a message might be returned such as "The fill volume for round 2 of the cycler mode must be within the range 250 mL to 1800 mL, please check the values you have entered in the prescription."

In some instances, the target HDM may perform compatibility checks prior to execution of the prescription treatment. A compatible prescription file may be stored in internal memory of the target HDM so that treatment can be performed. Thus, when creating a new prescription or updating an existing prescription, Unity aims to identify any prescriptions that would be incompatible with the target HDM to avoid poor user experience and workflow difficulties in the home.

A medical treatment machine such as a dialysis machine (e.g., a home dialysis machine [HDM]) can be configured to receive a digital prescription file that defines parameters of a medical treatment (e.g., a dialysis treatment) to be administered to a patient. The digital prescription file can be prepared and delivered in such a way that the medical treatment machine can confirm that the issuer of the digital prescription file is an authorized issuer. For example, the digital prescription file may be digitally signed by the issuer of the prescription. The signed digital prescription file is delivered to the medical treatment machine via a secured or unsecured medium. In addition to being digitally signed by the issuer, the digital prescription file can be encrypted. Upon receipt of the encrypted digital prescription file, the medical treatment machine can decrypt the digital prescription file. For further discussion of various implementations for securely distributing prescription files within a connected health system, references is made to U.S. application Ser. No. 15/497,529 filed Apr. 26, 2017, entitled "Securely Distributing Medical Prescriptions," which is incorporated herein by reference in its entirety.

In some implementations, the medical treatment machine may be a peritoneal dialysis machine. FIG. 1 shows an example of a PD system 100 that is configured to receive a digital prescription file. In some implementations, the PD system 100 is configured for use at a patient's home (e.g., a home PD system). The PD system 100 includes a PD machine 102 (also referred to as a PD cycler) seated on a cart 104. The PD machine 102 includes a housing 106, a door 108, and a cassette interface that contacts a disposable PD cassette when the cassette is disposed within a cassette compartment formed between the cassette interface and the closed door 108. A heater tray 116 is positioned on top of the housing 106. The heater tray 116 is sized and shaped to accommodate a bag of dialysate (e.g., a 5-liter bag of dialysate). The PD machine 102 also includes a user interface such as a touch screen 118 and control panel 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette via dialysate bag lines 126 and a heater bag line 128, respectively. The dialysate bag lines 126 can be used to pass dialysate from dialysate bags 122 to the cassette during use, and the heater bag line 128 can be used to pass dialysate back and forth between the cassette and the heater bag 124 during use. In addition, a patient line 130 and a drain line 132 are connected to the cassette. The patient line 130 can be connected to a patient's abdomen via a catheter and can be used to pass dialysate back and forth between the cassette and the patient's peritoneal cavity during use. The drain line 132 can be connected to a drain or drain receptacle and can be used to pass dialysate from the cassette to the drain or drain receptacle during use.

The touch screen 118 and the control panel 120 allow an operator to input various treatment parameters to the PD machine 102 and to otherwise control the PD machine 102. In addition, the touch screen 118 servers as a display. The touch screen 118 functions to provide information to the patient and the operator of the PD system 100. For example, the touch screen 118 may display information related to a dialysis treatment to be applied to the patient, including information related to a prescription, as described in more detail below.

The PD machine 102 includes a processing module 101 that resides inside the PD machine 102 and which is configured to communicate with the touch screen 118 and the control panel 120. The processing module 101 is configured to receive data from the touch screen 118 and the control panel 120 and control the PD machine 102 based on the received data. For example, the processing module 101 can adjust the operating parameters of the PD machine 102. In some implementations, the processing module 101 is an MPC823 PowerPC device manufactured by Motorola, Inc.

The PD machine 102 is configured to connect to a network 110. The PD machine 102 includes a transceiver 112 that is configured to facilitate the connection to the network 110. Other medical devices (e.g., other dialysis machines) may be configured to connect to the network 110 and communicate with the PD machine 102. Similarly, one or more remote entities, such as issuers of digital prescription files may be able to connect to the network 110 and communicate with the PD machine 102 in order to provide digital prescriptions for implementing on the PD machine 102.

Figure 4:
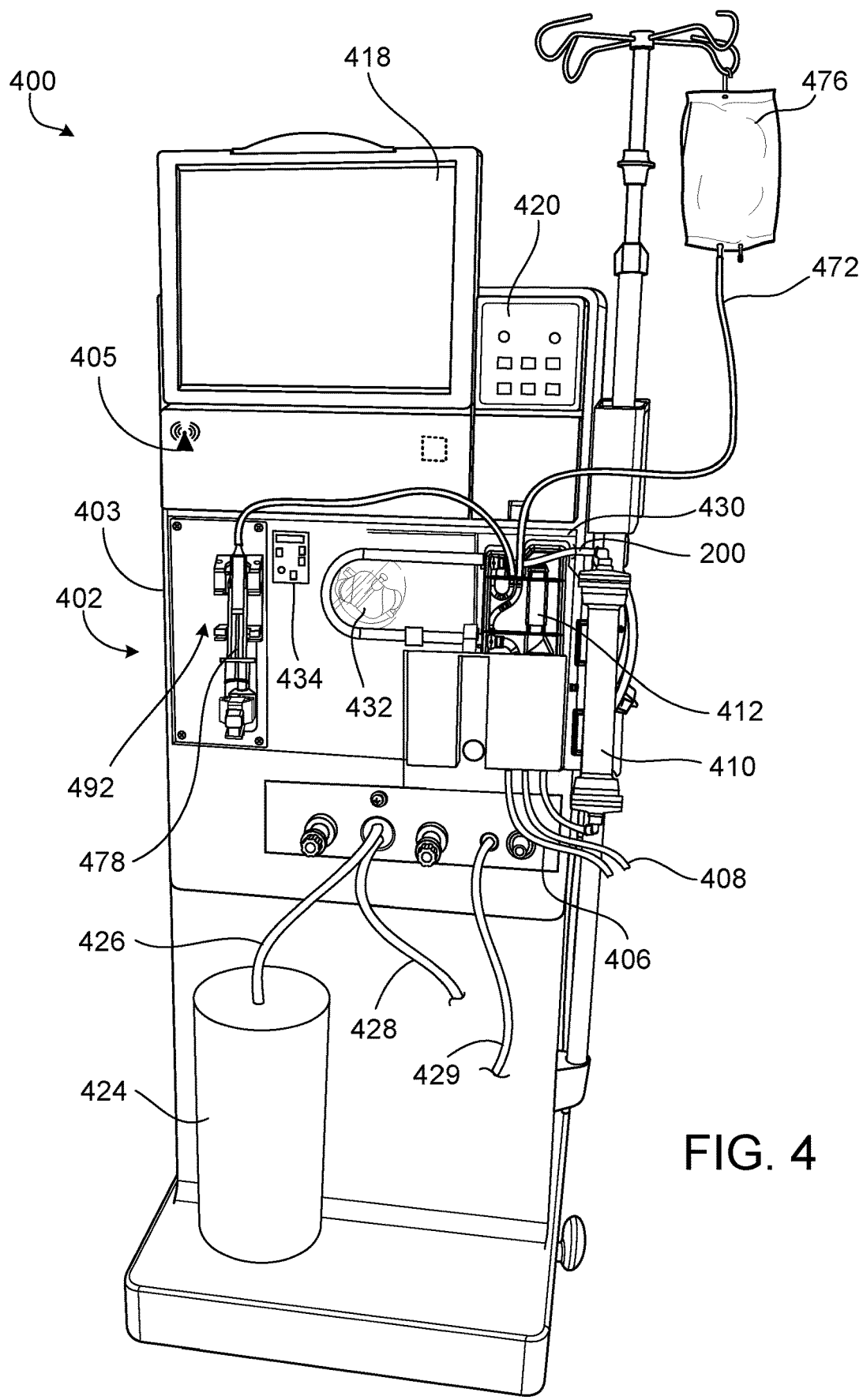
FIG. 4 is a front perspective view of a hemodialysis machine connected to a network.

In some implementations, a medical device 102 (e.g., the PD machine 102 of FIG. 1 and/or the HD machine 402 of FIG. 4) is configured to communicate with a connected health system (e.g., via the network 110 of FIG. 1 and/or the network 422 of FIG. 4).

Figure 2:
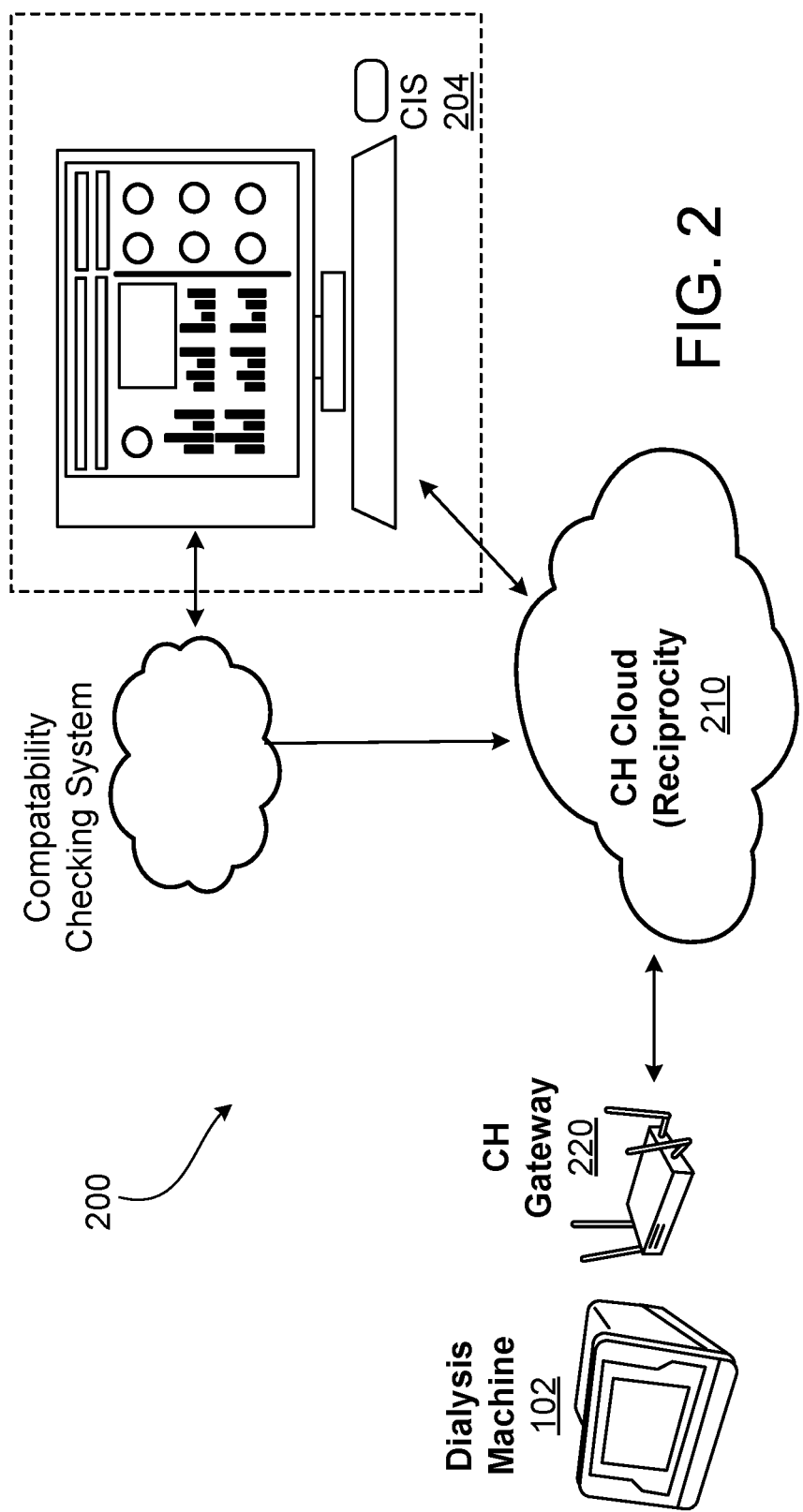
FIG. 2 is a schematic illustration showing an example of a connected health system (CHS) including infrastructure and servicing process flows for distributing digital prescriptions and checking prescription compatibility according to the system described herein.

FIG. 2 is a schematic illustration showing an example of a connected health system (CHS) 200 system that can include, among other things, a compatibility checking system 205, a CH cloud service 210 and a CH Gateway 220. The prescription compatibility checking system 205, an implementation of which may also be referred to herein as Unity, performs prescription compatibility checking services as discussed in detail herein. The CH cloud service 210, an implementation of which may also be referred to herein as Reciprocity, may be a cloud-based application that serves as a communication pipeline (e.g., facilitates the transfer of data) among components of the CHS service 200. The CH Gateway 220 may serve as a communication device (e.g., a standard communication device) among dialysis machines that are part of the CHS service 200. The CH Gateway 220 is in communication with the medical device 102 and the CH cloud service 210 and is configured to receive data from the CH cloud service 210 and provide the data to the medical device 102. In some examples, the digital prescription file is encrypted and then uploaded to the CH cloud service 210. In some implementations, prescription parameters of the digital prescription file (e.g. as a prescription parameters file) may be initially transmitted and checked for compatibility and/or otherwise processed by the prescription compatibility checking system 205 that may be part of the system or CIS of the provider 204 and/or provided by an Internet or cloud-based system before being uploaded to the CH cloud service 210. In some implementations, the prescription parameters file may be securely encrypted and transmitted between the CIS and Unity in a similar manner as provided for distribution of a digital prescription file. The medical device 102 may poll the CH cloud service 210 for available files (e.g., via the CH Gateway 220), and the medical device 102 may temporarily store available files for processing. In situations in which multiple digital prescription files are available on the CH cloud service 210, the medical device 102 may identify and implement newer digital prescription files (e.g., based on a date associated with the digital prescription file). Such date identification can allow the medical device 102 to implement up-to-date prescriptions (e.g., the most up-to-date prescriptions) associated with the particular patient. The patient may then follow a patient confirmation process to accept the digital prescription file before the prescription data is programmed into the medical device 102 for implementation.

In some implementations, the CH cloud service 210 may include a component that acts as a proxy for performing digital signature operations. For example, the CIS of the provider 204 may communicate with the CH cloud service 210 to authenticate itself. The communication between the medical device 102 and the CH cloud service 210 and/or the CIS of the provider 204 may be secured according to one or more cryptographic protocols. For example, Transport Layer Security ("TLS") may be employed to provide communications security over the network 110, 422. In some implementations, TLS employs encryption according to one or more standards, such as the Advanced Encryption Standard ("AES"). In some implementations, other data besides the digital prescription file may be exchanged among the components of the CHS service 200, including treatment data and/or device maintenance data transmitted between the medical device 102 and the CIS of the provider 204.

Figure 3:
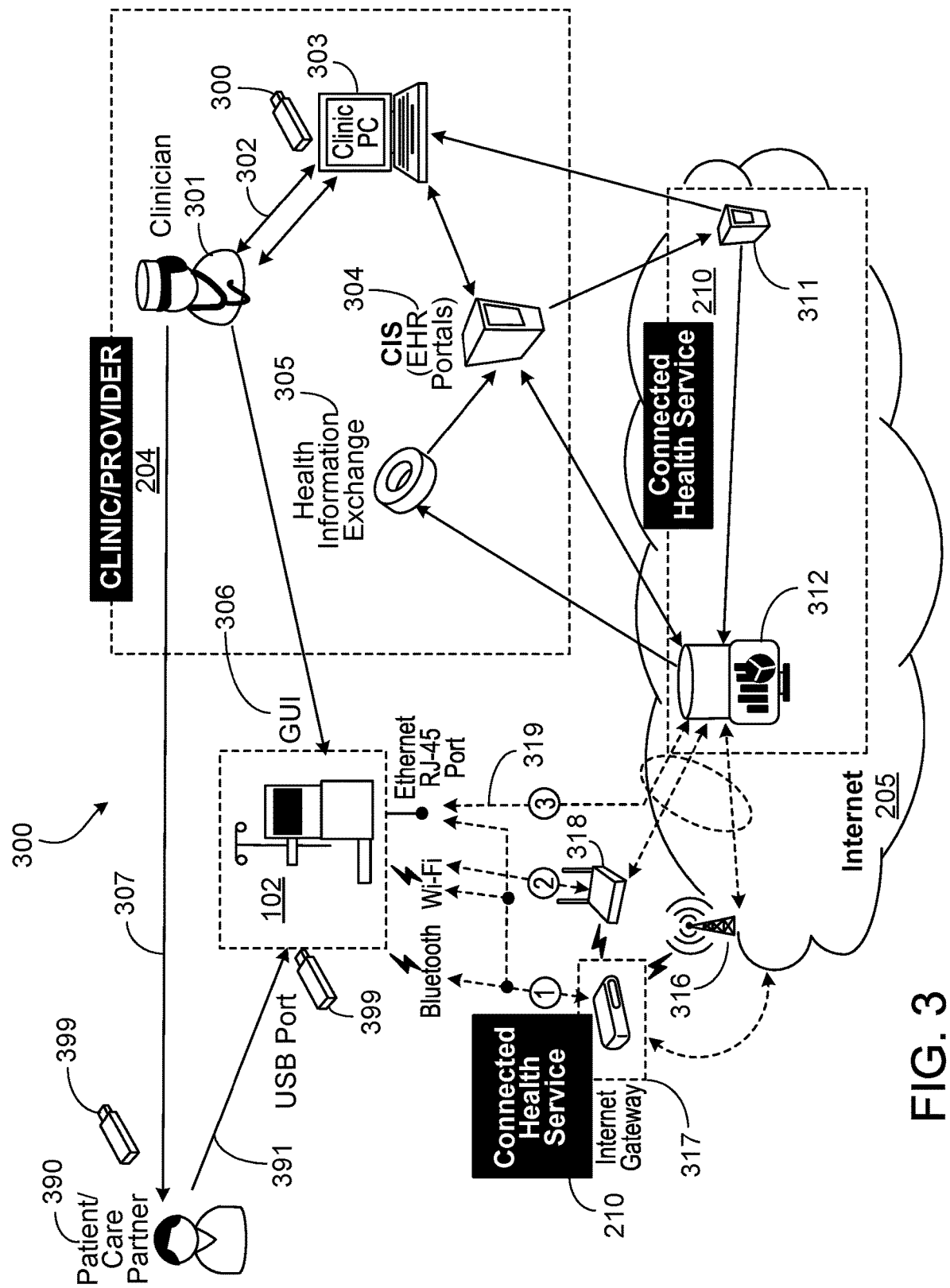
FIG. 3 is a schematic illustration showing an a more detailed view of an implementation of the CHS for provisioning digital prescriptions to a medical device.

FIG. 3 is a schematic illustration showing an example of a connected health system (CHS) provisioning digital prescriptions to a medical device 102 from a provider 204. FIG. 3 illustrates the provider 204 (i.e., a provider clinic) where a clinician 301 interacts (indicated by arrows 302) with a computer terminal 303 that is connected to a clinical information system (CIS) 304. The CIS 304 is connected via the internet to the connected health service 210, which is a cloud-based system including a web service computer server 311 containing a processor for conducting prescription compatibility operations (described in more detail herein) and an Internet of Things (IoT) cloud platform 312 configured to distribute digital prescriptions and configuration files to remote medical devices, such as an in-home medical device 102. The CIS 304 is also connected to a health information exchange 305 coordinating an electronic exchange of digital health care information between different providers 204 and the CIS 304.

FIG. 3 shows the IoT cloud platform 312 able to connect to the medical device 102 in different ways (as indicated by "1", "2", and "3"). In a first example connection method, the IoT cloud platform 312 of the connected health service 210 utilizes an existing cellular network 316 to broadcast data to an internet gateway 317 local to the medical device 102 and connected to the medical device 102 by, for example, a Bluetooth connection. In the second and third examples, the IoT cloud platform 312 sends data via the internet to the medical device 102 connected to the Internet either by a wireless device 318 or a wired connection 319.

In operation, the clinician 301 enters a medical prescription onto the computer terminal 303 for a given patient 390 for use in conducting a medical procedure with the medical device 102. With the medical prescription entered into the computer terminal 303, the prescription information is passed into the provider's 204 own CIS 304 system, where it is submitted to the web service computer server 311 of the CH cloud service 210. The web service server 311 determines if the submitted medical prescription is compatible with the patient's medical device 102, as further discussed in detail herein, and returns an indication to the provider's 204 computer terminal 303 that informs the clinician 301 if the entreated medical prescription is compatible with the patient's 390 medical device 102. If the medical prescription is not compatible, in some instances, the CHS provides information to the computer terminal 303 to information the clinician 301 what aspect of the medical prescription was incompatible and why. In some instances, upon receiving confirmation that the medical prescription is compatible with the medical device 102, the clinician 301 instructs the CH cloud service 210 to send the medical prescription to the patient's medical device 102. In some instances, upon receiving confirmation that the medical prescription is compatible with the medical device 102, the clinician 301 manually configures the medical device 102 via a graphical user interface (GUI) 306. In other instances, upon receiving confirmation that the medical prescription is compatible with the medical device 102, the clinician 301 downloads the medical prescription and a configuration file for operating the medical device onto on a portable external device such as a flash drive 399 or other transportable storage medium. The flash drive 399 can be given to the patient 390 at the provider 204 (i.e., clinic) for the patient 390 or the patient's care partner to load the configuration file onto the medical device 102 directly (as indicated by arrow 391).

While certain implementations have been described, other implementations are possible.

While the medical device (e.g. a dialysis machine) has been described as communicating with remote entities through the network, in some implementations, the dialysis machine is configured to communicate directly with remote entities. For example, the transceiver may be configured to facilitate a direct connection between the dialysis machine and a remote entity, such as an issuer of a digital prescription file and/or a certificate authority.

While the systems and techniques described herein have been largely described with reference to a dialysis machine, and in particular, a PD machine, other types of medical treatment systems and/or machines may also use the systems and techniques to transmit digital prescription files and verify the compatibility of the digital prescription files with the patient's medical device. Examples of other medical treatment systems that may employ the techniques described herein include hemofiltration systems, hemodiafiltration systems, apheresis systems, cardiopulmonary bypass systems, and hemodialysis ("HD") systems. In some implementations, the medical treatment system (e.g., medical device 102) is a dialysis machine configured for use at a patient's home (e.g., a home dialysis machine ("HDM")). The HDM can take the form of a home PD machine or a home hemodialysis ("HD") machine.

FIG. 4 shows an HD system 400 that is configured to receive a digital prescription file in a manner similar to that described above. In some implementations, the HD system 400 is configured for use at a patient's home (e.g., a home HD system). The HD system 400 includes an HD machine 402 to which a disposable blood component set 404 that forms a blood circuit is connected. During hemodialysis, arterial and venous patient lines 406, 408 of the blood component set 404 are connected to a patient and blood is circulated through various blood lines and components, including a dialyzer 410, of the blood component set 404. At the same time, dialysate is circulated through a dialysate circuit formed by the dialyzer 410 and various other dialysate components and dialysate lines connected to the HD machine 402. Many of these dialysate components and dialysate lines are located inside the housing 403 of the HD machine 402, and are thus not visible in FIG. 4. The dialysate passes through the dialyzer 410 along with the blood. The blood and dialysate passing through the dialyzer 410 are separated from one another by a semi-permeable structure (e.g., a semi-permeable membrane and/or semi-permeable microtubes) of the dialyzer 410. As a result of this arrangement, toxins are removed from the patient's blood and collected in the dialysate. The filtered blood exiting the dialyzer 410 is returned to the patient. The dialysate that exits the dialyzer 410 includes toxins removed from the blood and is commonly referred to as "spent dialysate." The spent dialysate is routed from the dialyzer 410 to a drain.

One of the components of the blood component set 404 is an air release device 412. The air release device 412 includes a self-sealing vent assembly that allows air to pass through while inhibiting (e.g., preventing) liquid from passing through. As a result, if blood passing through the blood circuit during treatment contains air, the air will be vented to atmosphere as the blood passes through the air release device 412.

As shown in FIG. 4, a dialysate container 424 is connected to the HD machine 402 via a dialysate supply line 426. A drain line 1428 and an ultrafiltration line 429 also extend from the HD machine 402. The dialysate supply line 426, the drain line 428, and the ultrafiltration line 429 are fluidly connected to the various dialysate components and dialysate lines inside the housing 403 of the HD machine 402 that form part of the dialysate circuit. During hemodialysis, the dialysate supply line 426 carries fresh dialysate from the dialysate container 424 to the portion of the dialysate circuit located inside the HD machine 402. As noted above, the fresh dialysate is circulated through various dialysate lines and dialysate components, including the dialyzer 410, that form the dialysate circuit. As the dialysate passes through the dialyzer 410, it collects toxins from the patient's blood. The resulting spent dialysate is carried from the dialysate circuit to a drain via the drain line 428. When ultrafiltration is performed during treatment, a combination of the spent dialysate and excess fluid drawn from the patient is carried to the drain via the ultrafiltration line 429.

The blood component set 404 is secured to a module 430 attached to the front of the HD machine 402. The module 430 includes a blood pump 432 capable of driving blood through the blood circuit. The module 430 also includes various other instruments capable of monitoring the blood flowing through the blood circuit. The module 430 includes a door that when closed, as shown in FIG. 4, cooperates with the front face of the module 430 to form a compartment sized and shaped to receive the blood component set 404. In the closed position, the door presses certain blood components of the blood component set 404 against corresponding instruments exposed on the front face of the module 430. Such an arrangement facilitates control of the flow of blood through the blood circuit and monitoring of the blood flowing through the blood circuit.

The blood pump 432 can be controlled by a blood pump module 434. The blood pump module 434 includes a display window, a start/stop key, an up key, a down key, a level adjust key, and an arterial pressure port. The display window displays the blood flow rate setting during blood pump operation. The start/stop key starts and stops the blood pump 432. The up and down keys increase and decrease the speed of the blood pump 432. The level adjust key raises a level of fluid in an arterial drip chamber.

A drug pump 492 also extends from the front of the HD machine 402. The drug pump 492 is a syringe pump that includes a clamping mechanism configured to retain a syringe 478 of the blood component set 404. The drug pump 492 also includes a stepper motor configured to move the plunger of the syringe 478 along the axis of the syringe 478. A shaft of the stepper motor is secured to the plunger in a manner such that when the stepper motor is operated in a first direction, the shaft forces the plunger into the syringe 478, and when operated in a second direction, the shaft pulls the plunger out of the syringe 478. The drug pump 492 can thus be used to inject a liquid drug (e.g., heparin) from the syringe 478 into the blood circuit via a drug delivery line 474 during use, or to draw liquid from the blood circuit into the syringe 478 via the drug delivery line 474 during use.

The HD machine 402 includes a touch screen 418 and a control panel 420. The touch screen 418 and the control panel 420 allow an operator to input various treatment parameters to the HD machine 402 and to otherwise control the HD machine 402. In addition, the touch screen 418 serves as a display. The touch screen 418 functions to provide information to the patient and the operator of the HD system 400. For example, the touch screen 418 may display information related to a dialysis treatment to be applied to the patient, including information related to a prescription, as described above. The HD machine 402 includes a processing module 401 that resides inside the machine and which is configured to communicate with the touch screen 418 and the control panel 420. The processing module 401 is configured to receive data from the touch screen 418 and the control panel 420 and control the HD machine 402 based on the received data. For example, the processing module 401 can adjust the operating parameters of the HD machine 402.

The HD machine 402 is configured to connect to a network 422. The HD machine 402 includes a transceiver 405 that is configured to facilitate the connection to the network 422. Other medical devices (e.g., other dialysis machines) may be configured to connect to the network 422 and communicate with the HD machine 402. Similarly, one or more remote entities, such as issuers of digital prescription files may be able to connect to the network 422 and communicate with the HD machine 402 in order to provide digital prescriptions for implementing on the HD machine 402, as described above.

Figure 5:
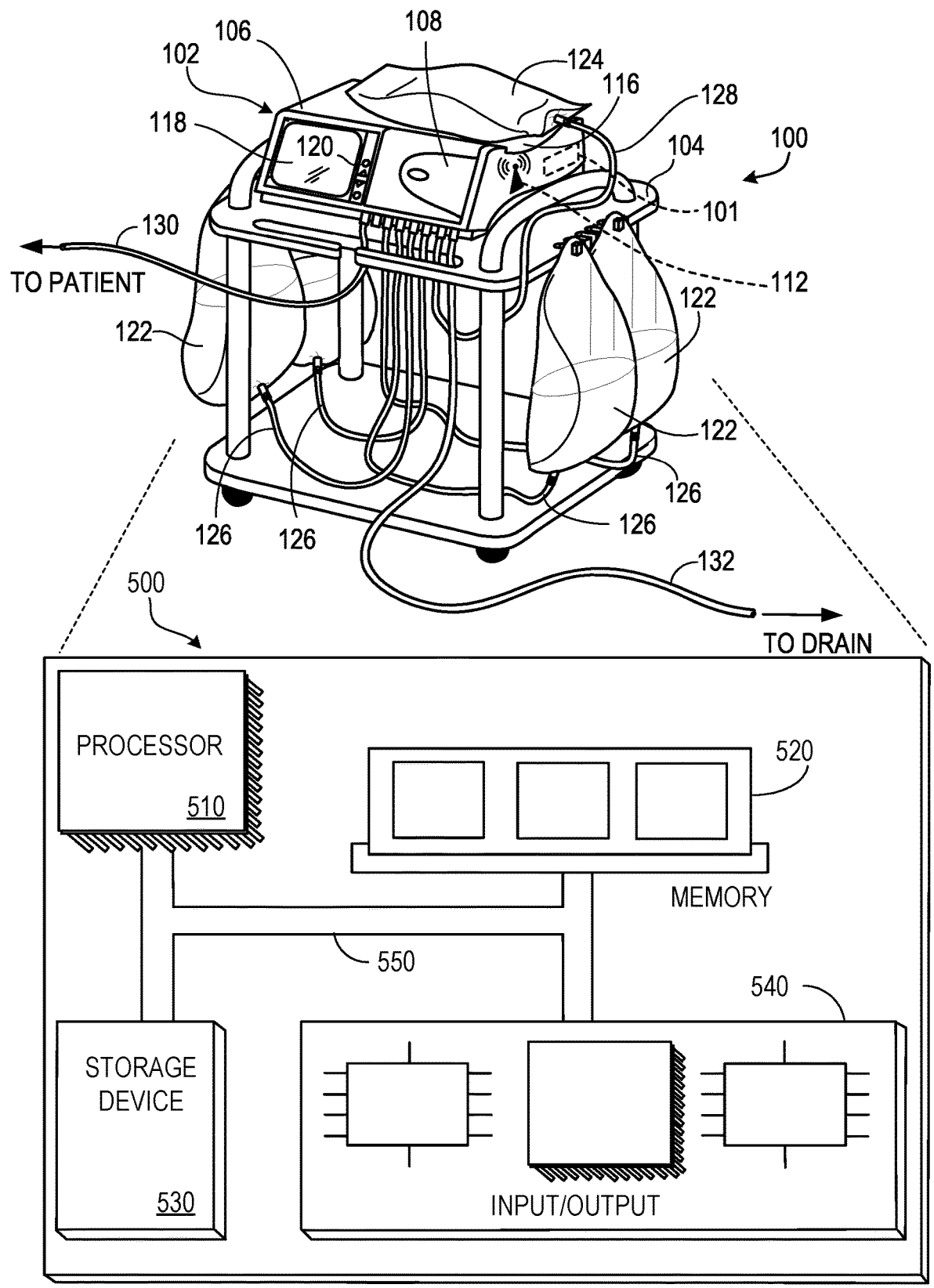
FIG. 5 is a block diagram of an example medical device computer system.

FIG. 5 is a block diagram of an example computer system 500. For example, referring to FIGS. 1 and 4, the processing modules 101, 401 could be examples of the system 500 described here. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. The processor 510 can be a single-threaded processor, a multi-threaded processor, or similar device. The processor 510 is capable of processing instructions stored in the memory 520 or on the storage device 530. The processor 510 may execute operations such as causing the dialysis system to carry out functions related to a dialysis treatment according to a prescription received in a digital prescription file.

The memory 520 stores information within the system 500. In some implementations, the memory 520 is a computer-readable medium. The memory 520 can, for example, be a volatile memory unit or a non-volatile memory unit. In some implementations, the memory 520 stores information related to patients' identities.

The storage device 530 is capable of providing mass storage for the system 500. In some implementations, the storage device 530 is a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network. In some implementations, the information stored on the memory 520 can also or instead be stored on the storage device 530.

The input/output device 540 provides input/output operations for the system 500. In some implementations, the input/output device 540 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 540 includes driver devices configured to receive input data and send output data to other input/output devices, e.g., a keyboard, a printer, and display devices (such as the touch screen 118, 418). In some implementations, mobile computing devices, mobile communication devices, and other devices are used.

In some implementations, the system 500 is a microcontroller. A microcontroller is a device that contains multiple elements of a computer system in a single electronics package. For example, the single electronics package could contain the processor 510, the memory 520, the storage device 530, and input/output devices 540.

Figure 6:
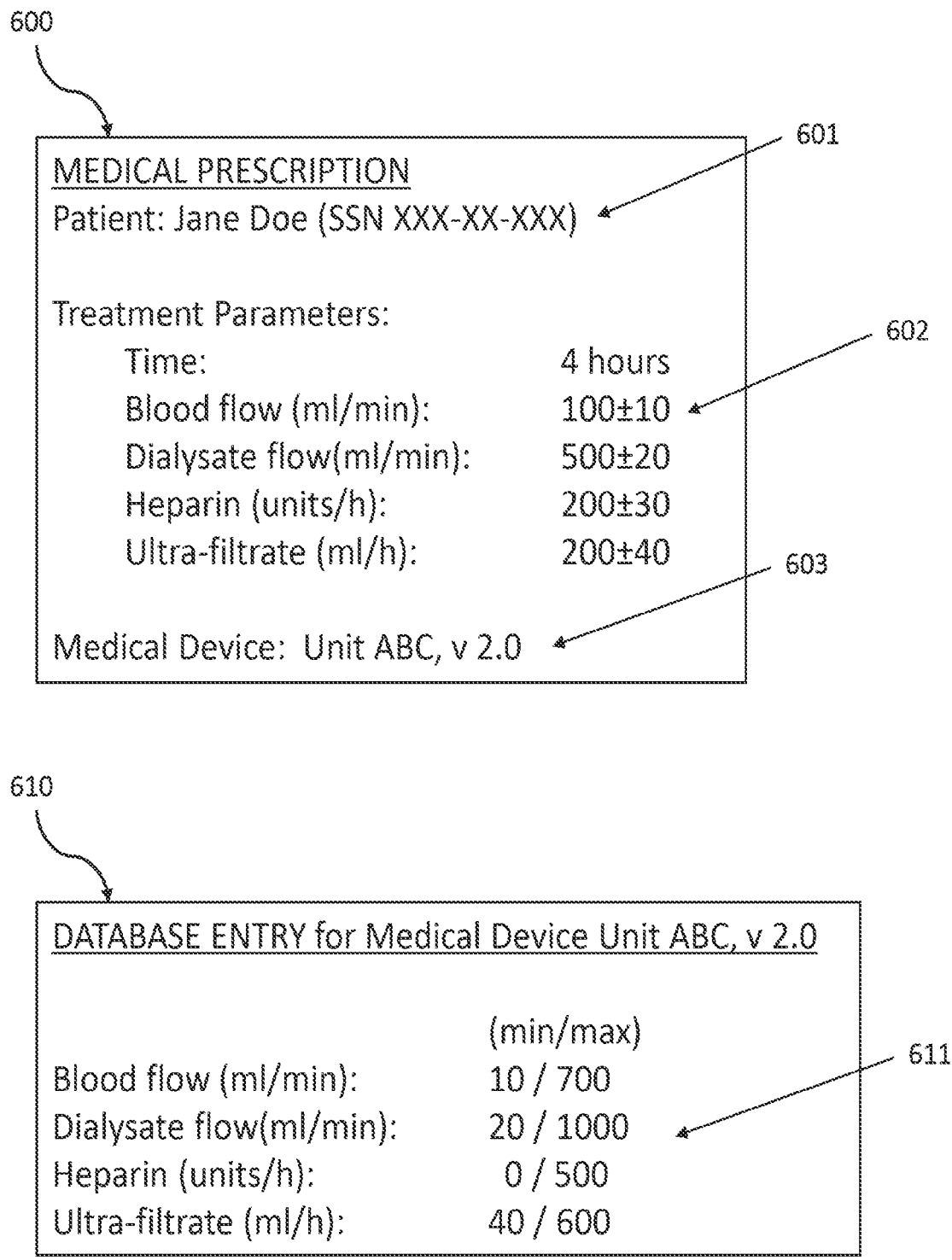
FIG. 6 illustrates examples of a digital prescription file and a database entry for a medical device.

FIG. 6 is an illustrative examples of a prescription parameters file 600 representing a prescription written by a clinician for a patient and a database entry 610 for a medical device 102 (e.g., dialysis machine 102 of FIG. 1). Where the reference "102" is used generally to refer to a medical device 102.

The prescription parameters file 600 can include treatment parameters 602, which in some implementations can be in plaintext format. In some instances, the medical device 102 is a dialysis system and the prescription is usable by the dialysis system 100 to perform a dialysis treatment. The prescription parameters file 600 can include patient identification 601 such as a Patient ID, a serial number (e.g., identification 603) of a cycler (e.g., medical device 102) to be used, information related to a date and time at which the cycler was assigned to the patient, an ID associated with the patient's provider (e.g., issuer), an ID associated with the patient's clinic, the patient's first and last name, a minimum peritoneal volume of the patient, and a maximum peritoneal volume of the patient. In some implementations, the prescription parameters file 600 can contain multiple sets of treatment parameters 602 (e.g., six prescriptions) for the patient. The prescription parameters file 600 can include a date/time stamp identifying a time at which each prescription was created and/or assigned to the patient.

The prescription parameters file 600 also includes attributes related to each prescription. For example, the prescription may have attributes related to a prescription sequence ID, a prescription ID, a name (e.g., to be displayed on the medical device 102), a type for a disposable line set to be used when providing the treatment (e.g., "low feature," "medium feature," "high feature"), a quality of a catheter to be used when providing the treatment (e.g., "slow," "average," "fast"), a flow rate to be used during the fill phase of a cycle, a flow rate to be used during the drain phase of a cycle, and a requested time at which the treatment is to end.

Within the parameters of a prescription, a patient 390 can have one or more rounds of treatment. Each round can have one cycle or multiple repeating cycles. Repeating cycles within a particular round may have the same settings. In some implementations, the prescription parameters file 600 includes attributes related to the particular prescription round and/or cycle, such as a prescription round ID (e.g., giving the position of the round in the treatment sequence), a number of cycles included in a particular round, a cycle type code (e.g., "cycler," "manual," "PD+," "last fill"), a requested fill volume for each cycle in the round, a requested dwell time for each cycle in the round, an expected ultra-filtration volume for each cycle in the round, a drain mode (e.g., "standard," "complete"), and a requested drain volume for each cycle in the round. In some implementations, the prescription parameters file 600 also includes attributes related to a type of bag prescribed for a particular treatment.

The database entry 610 can include operational parameters 611 of the specific medical device having an identification 603 in the database entry 610. The operational parameters 611 can include, for example, minimum and maximum operational rates for various device operations, such as blood flow, dialysate flow, drug delivery rates (e.g. heparin, dextrose), and ultra-filtrate flow rates.

FIG. 7 is a flowchart illustrating a serious of operations executed by a prescription compatibility checking system 205 (FIG. 2) for checking the compatibility of a medical prescription with a patient's 390 home medical device 102 (FIG. 1). In a first step, the prescription compatibility system 205 (FIG. 2) receives 710 prescription parameters of a medical prescription e.g., a prescription parameters file 600) from a CIS 304 (FIG. 3), which can include a patient identification 601 (FIG. 6) and treatment parameters 602 (FIG. 6) for use in performing a medical procedure on the patient 390 (FIG. 3) using a medical device 102 (FIG. 1). Next, the prescription compatibility checking system 205 (FIG. 2) accesses 720 a database on a server 311 (FIG. 3) containing the operational parameters 611 (FIG. 6) of a plurality of medical devices, including the medical device 102 (FIG. 1) to be used on the patient 390 (FIG. 3). The prescription compatibility checking system 205 performs the compatibility check 730 on the treatment parameters 602 from the patient's prescription parameters file 600 to the operational parameters 611 (FIG. 6) of the patient's medical device 102 in the database. Based on the comparison, the prescription compatibility checking system 205 (FIG. 2) generates 740 a prescription compatibility response that indicates if the treatment parameters 602 of the prescription 600 are able to be executed by the patient's medical device 102. Finally, the CHS 210 provides the prescription compatibility response to the CIS 304 in order for a clinician 301 to approve transmission or delivery of the prescription 600 to the medical device 102.

In some instances, the prescription parameters file 600 comprises an identification 603 of the patient's medical device for use in conducting the medical procedure. In some instances, the database containing operational parameters of the plurality of medical devices, includes a plurality of identifications of medical devices associated with a corresponding plurality of patients including an identification of a medical device associated with the received patient information. And the CH cloud service 210 confirms, based on the received patient identification 601, the identification 603 of the patient's medical device at the patient's home based on the identification of the medical device 102 associated with the received patient information in the database.

In some instances, the CHS 210 calculates a simulated outcome of the medical procedure based on the received patient medical prescription of the prescription parameters file 600 and the operational parameters 611 of the patient medical device 102. In this instance, generating 740 the prescription compatibility response includes determining if the simulated outcome of the medical procedure satisfies one or more of: the prescription parameters file 600, the patient treatment limitations, and the operational parameters 611 of the medical device 102.

In some instances, upon instruction from the clinician 301, and after a received prescription parameters file 600 is indicated as compatible, the CH cloud service 210 transmits the medical prescription via the Internet 205 to the medical device 102 (as detailed above in FIG. 3).

In some instances, the CH cloud service 210 sends the prescription parameters file 600 via the Internet 205 to the patient's 390 email address to allow the patient 390 to manually load the prescription parameters file 600 into the medical device 102.

Figure 8:
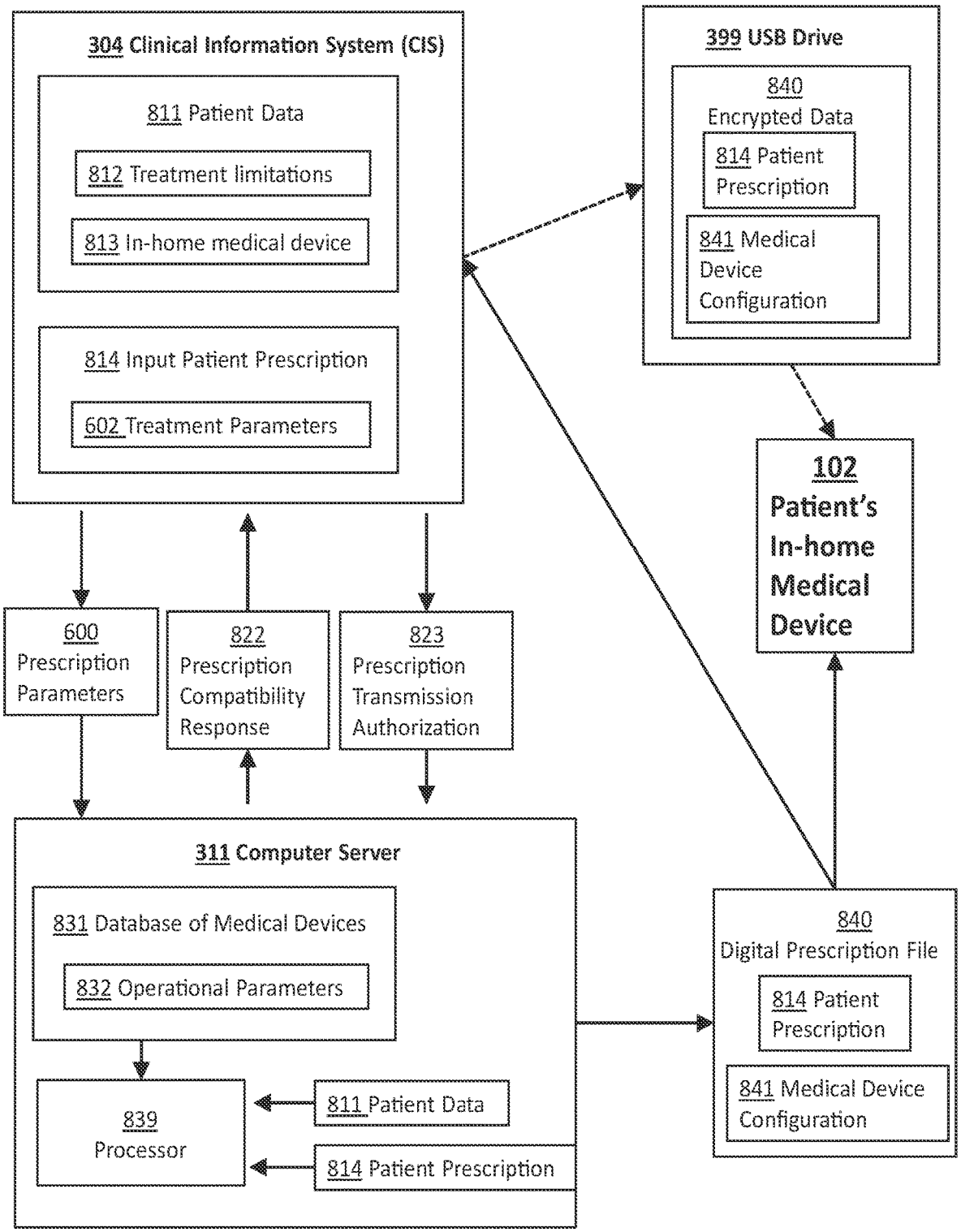
FIG. 8 illustrates an example technique for verifying the compatibility of a digital prescription file and delivering the digital prescription file to the patient's home medical device.

FIG. 8 illustrates an example technique for verifying the compatibility of a digital prescription file and delivering the digital prescription file to the patient's home medical device. In FIG. 8, a CIS 304 communicates via the Internet with a computer server 311 of a CHS 201 (FIG. 2) in order to check the compatibility of a prescription parameters file 600 created to use in conducting a medical procedure using a medical device 102 configured to receive a digital medical prescription. In operation, a clinician 301 (FIG. 3) inputs a patient prescription 814 via a computer terminal 303 (FIG. 3) connected to the CIS, where the input patient prescription 814 includes treatment parameters 602 for conducting the medical procedure with the patient's medical device 102. The CIS may already include a patient data file 811 which stores certain basic information regarding the patient 390 (FIG. 3), for example, any treatment limitations 812 and/or an identification 813 of the specific medical device 102 (e.g. the HDM at the patient's home) for use in conducting the medical procedure on the patient 390. With a new patient prescription 814 entered into the computer terminal 303, the CIS generates a prescription parameters file 600 and provides the prescription parameters file 600 to the computer server 311. The computer server 311 includes a processor 839 and has access to a database 831 of medical devices storing the operational parameters 611 of the medical devices in the database 831. In some implementations, the database 831 is stored on the computer server 311 whereas in other implementations the computer server 311 may access the database 831 remotely. First, the process receives the prescription parameters file 600 representing the patient prescription 814 with treatment parameters 602 that includes the identification 813 of the patient's medical device and retrieves the operational parameters 611 of the patient's medical device 102 from the database 831 of medical devices.

Next, the processor 839 compares the operational parameters 611 of the patient's medical device 102 to the treatment parameters 602 in the received patient prescription 814 from the prescription parameters file 600 and determines if the treatment parameters 602 are compatible with the medical device 102 according to the operational parameters 611 in the database 831. In some instances, the processor determines if values of specific treatment parameters 602 are within ranges specified by the operational parameters 611 of the specific medical device 102. In some instances, the computer server 311 also receives patient treatment limitations 812 from the CIS 304. In some instances, the processor 839 uses the patient prescription 814 to calculate an outcome of the medical treatment procedure specified by the treatment parameters 602 and compares the treatment outcome to one or both of the treatment limitations 812 and the operational parameters 611 to determine if the patient prescription 814 is compatible with the medical device 102 and the patient 390. If the computer server 311 determines that the patient prescription 814 is compatible with the patient's medical device 102, as described above, then the computer server 311 provides a prescription compatibility response 822 to the CIS 304. In some instances, the prescription compatibility response 822 is a binary indication of whether or not the treatment parameters of the prescription parameters file 600 can be conducted within the operational parameters 611 of the medical device 102. In some instances, the prescription compatibility response 822 includes specific confirmations for each value provided in the treatment parameters 602 of the patient prescription 814. If the computer server 311 determines that the patient prescription 814 is not compatible with either the patient 390 or the patient's medical device 102, the prescription compatibility response 822 provided to the CIS 304, in some instances, indicates which values of the patient prescription 814 were determined to be incompatible with the patient 390 or the patient's medical device 102.

Once the CIS 304 has received the prescription compatibility response 822 from the computer server 311, the CIS relays the prescription compatibility response 822 (or some general indication) to the computer terminal 303 where the clinician 301 is then able to instruct the CIS to provide a prescription transmission authorization 823 to the computer server 311 in order to instruct the computer server 311 to transmit the patient prescription 814 to the patient's medical device 102 (as described above in FIG. 3). In operation, after determining appropriate compatibility, the computer server 311 may transmit the prescription parameters file 600 to the connected health system, as further discussed elsewhere herein, that generates a digital prescription file 840 based on the received prescription parameters 600. In some instances, the digital prescription file 840 may be a set of computer-readable instructions for programming the patient's medical device 102 to conduct the medical treatment specified by the patient prescription 814. In some instances, the digital prescription file 840 is securely transmitted via the CHS cloud to the HDM as an encrypted data file, which, in some instances, also contains the patient prescription 814 in order to display the patient prescription 814 on a display of the patient's medical device 102. In some instances, when the CIS 304 receives a prescription compatibility response 822, the clinician 301 may send a prescription transmission authorization 823 which instructs the computer server 311 to receive the digital prescription file 840 from the connected health system in order for the clinician to download the digital prescription file 840 onto, for example, a flash drive 399 (FIG. 3), which enables the clinician 301 to provide a physical copy of the digital prescription file 840 to the patient 390 in order for the patient 390 to manually load the digital prescription file 840 onto their medical device 102.

File Processing

The file processing described below assumes that the system is supplied with prescription parameter files from the CIS with certificates included. If it is decided that the data passed from CIS is in a format that cannot be consumed by the target HDM, the file processing service shall play a role in creating the required files in an appropriate format. Furthermore, Unity may need to write certificates to a file.

The user issues an instruction through the CIS to send prescription parameter files to Unity which calls the CHS to verify that the service provider is an authorized user of Unity and/or CHS. The prescription parameter files are retrieved from the system record and sent through the secure connection and are passed through the compatibility checks. All individual prescriptions that are contained in the prescription set are checked. If the prescription parameter file compatibility checks pass, the file processing service may make a request to the CHS cloud (e.g. Reciprocity) to encrypt and sign the respective files to generate a digital prescription file. If encryption and signature process is successful, CHS issues a version ID for the files. The CHS may check the validity of certificates, e.g. trusted source, expiry date etc. CHS (Reciprocity) may store files on its cloud ready for download to the gateway or USB drive. In the process of sending files to the CHS (Reciprocity) cloud, there may be the option to save the files to USB drive. A request shall be made by the client to pull the latest 'program settings file' from CHS (Reciprocity). The calls the CHS to verify that the service provider is an authorized user of Unity and CHS. The user shall insert an approved USB drive. The clinic's workstation writes the 'configuration file' and the 'Prescription file' to the USB drive. A confirmation is supplied to the user if the 'configuration file' and the 'Prescription files' are written successfully to the USB drive.

Figure 9:
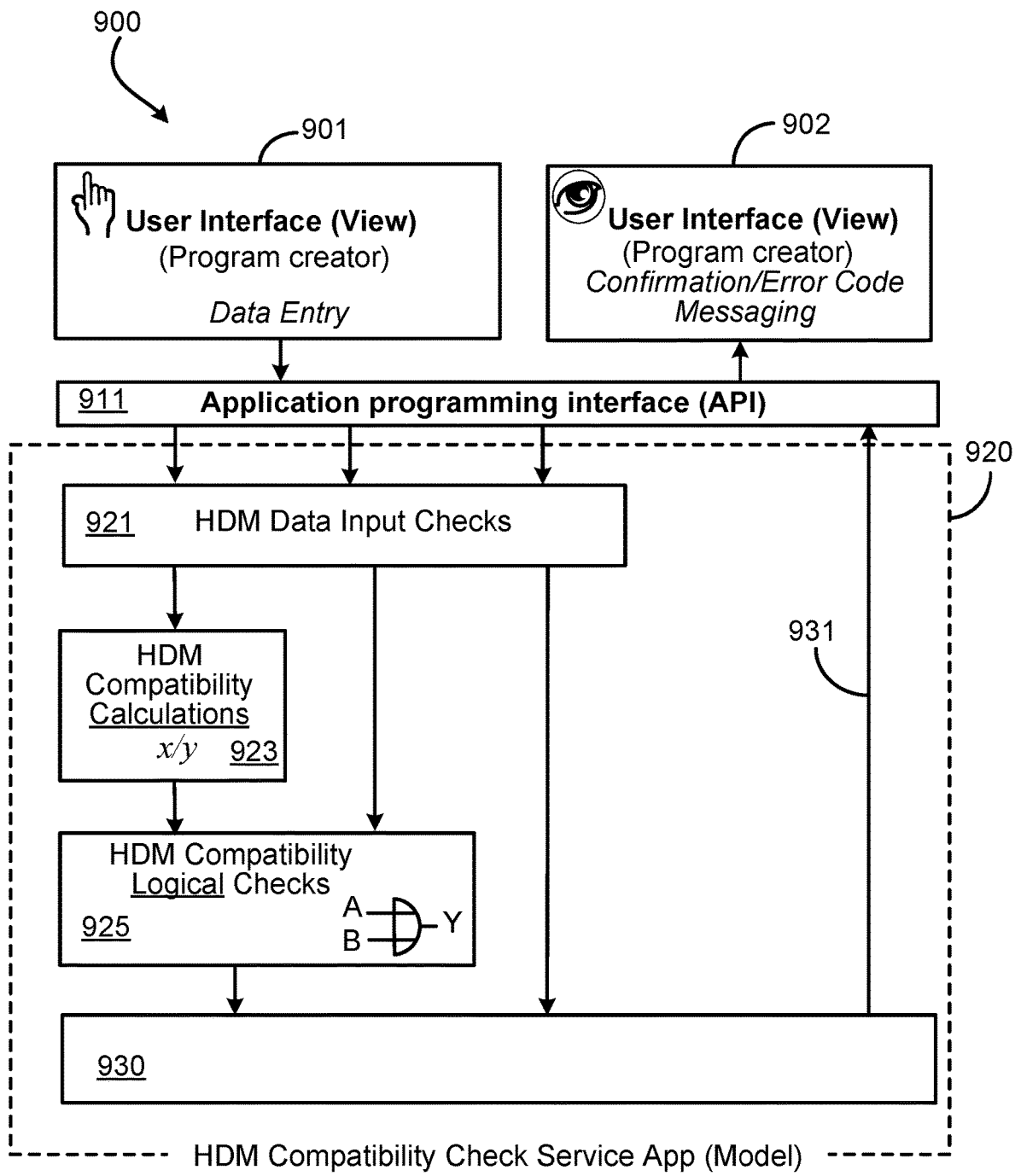
FIG. 9 illustrates an example technique for checking the compatibility of a digital prescription file.

FIG. 9 illustrates an example technique for checking the compatibility of a digital prescription file. FIG. 9 shows a diagram 900 of the operational elements of aspects of the present disclosure. A user interface 901 is provided on the computer terminal 303 in the clinic of the provider 204, and enables a patient prescription 814 to be created or entered into the CIS 304. Data entry in the user interface 901 enables the user to enter or retrieve program settings from the patient's electronic health record. Additionally, the user interface 901 of the computer terminal 303 can operate as a viewer 902 to display a confirmation to the clinician 301 of an indication that a provided patient prescription 814 is compatible with the patient's medical device 102, or to display one or more error codes if the computer server 311 determines that the patient prescription 814 is not compatible with the patient's medical device 102. The viewer 902 enables display of confirmation or error code messages, and translates any error code into an appropriate message so that the user made rectify the error. The CIS 304 provides the patient prescription 814 to a computer server 311 of the CH cloud service 210, as described above. On the computer server 311, a service application 920 that may, in some instances, interface with an API 911 on the computer terminal 303 in order to receives the patient prescription 814. The API 911 exposes services through which the client may submit program setting data and control how the compatibility checks are invoked. The processor 839 of the computer server 311 executes a prescription compatibility check model 920.

The prescription compatibility check model 920 includes a data input check 921, a compatibility calculation 923, a compatibility logical check 925, and a response generator 930. The data input check 921 applies to all variables passed through the API 911 which include data type, format, range, default values, allowable values, resolution and units of measure. For example, a particular variable may be a measurement of weight expressed in grams as an integer and with a range from 10,000 to 250,000. The HDM compatibility calculation 923 implements equations involving one or more variables that determine, for example, the total volume of fluid applied to a patient in a treatment or the time required to deliver a treatment from specific program settings supplied. The HDM compatibility logical checks 925, in some instances, check that the output of a calculation is below a threshold (e.g. treatment time <24 hours), or involve some combinatorial logic (e.g. if flow rate >100 mL/Min & Option 1 has been selected then calculated time for a treatment segment <1 hour). The confirmation/exception response generator 930 returns 931 a confirmation to the user if all compatibility checks pass successfully. If any compatibility checks fail, an exception response is generated containing an error code enabling the source of the error to be identified.

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations of the invention have been described. Nevertheless, it will be understood that various modifications may be made without departing from the spirit and scope of the invention. Accordingly, other implementations are within the scope of the following claims.

What is claimed is:
1. A connected health system comprising:
 a cloud-based application that facilitates data transfer between components of the system via a network;
 a remote medical device, wherein the remote medical device is configured to receive data from the cloud-based application;
 a database containing operational parameters of a plurality of medical devices, including operational parameters of the remote medical device;

a clinical information system configured to receive prescription parameters from a clinician;

a computer server comprising a processor configured for:

receiving, from the clinical information system, a digital prescription file comprising prescription parameters for use in conducting a medical procedure on a patient using the remote medical device;

identifying the operational parameters of the remote medical device from the database;

performing a compatibility check by comparing values of the prescription parameters of the digital prescription file to ranges determined by the operational parameters of the remote medical device;

generating, based on the compatibility check, a prescription compatibility response indicating if the prescription parameters are able to be executed by the remote medical device in order to conduct the medical procedure;

providing the prescription compatibility response to the clinical information system; and based on the compatibility check:

causing the remote medical device to perform a medical treatment based on the prescription parameters, or denying an authorization to transmit the prescription parameters to the remote medical device.

2. The system of claim 1, wherein the remote medical device is a peritoneal dialysis machine.

3. The system of claim 1, wherein the remote medical device is a hemodialysis machine.

4. The system of claim 1, wherein the digital prescription file comprises patient treatment limitations.

5. The system of claim 4, wherein generating the prescription compatibility response comprises determining if the prescription parameters are able to be executed by the remote medical device in order to conduct the medical procedure within the patient treatment limitations.

6. The system of claim 1, wherein the digital prescription file comprises an identification of the remote medical device for use in conducting the medical procedure.

7. The system of claim 6, wherein the database includes the operational parameters of the remote medical device identified in the digital prescription file.

8. The system of claim 6, wherein the database includes a plurality of identifications respectively associated with the plurality of medical devices and respectively associated with a plurality of patients, the plurality of identifications including the identification of the remote medical device, wherein the processor is further configured for:

confirming based on the identification of the patient, the identification of the remote medical device at the patient's home.

9. The system of claim 8, wherein generating the prescription compatibility response is further based on the confirming.

10. The system of claim 6, wherein the processor is further configured for:

calculating a simulated outcome of the medical procedure based on the prescription parameters and the operational parameters of the remote medical device, wherein generating the prescription compatibility response comprises determining if the simulated outcome of the medical procedure satisfies one or more of the prescription parameters, patient treatment limitations, and the operational parameters of the remote medical device.

11. The system of claim 1, wherein the prescription compatibility response indicates whether the prescription parameters are compatible or not compatible with the patient and whether the received prescription parameters are compatible or not compatible with the remote medical device.

12. The system of claim 11, wherein the processor is further configured for:

accepting the digital prescription file based on the prescription compatibility response.

13. The system of claim 12, wherein the remote medical device is configured to receive the digital prescription file via the network for use in conducting the medical procedure according to the prescription parameters.

14. The system of claim 12, wherein the processor is further configured for:

sending the digital prescription file via the network to a patient's email address for use in conducting the medical procedure according to the prescription parameters.

15. The system of claim 11, wherein the processor is further configured for:

denying the digital prescription file based on the prescription compatibility response.

16. The system of claim 15, wherein the processor is further configured for:

sending information regarding a denial of the digital prescription file via the network to the clinical information system.

17. The system of claim 1, wherein:

the system further comprises a removable physical storage device configured to interface with a terminal of the clinical information system; and the processor is further configured for providing, based on the prescription compatibility response, a signal via the network to the clinical information system for use in enabling a user of the clinical information system to download the digital prescription file onto the removable physical storage device interfaced with the terminal, the removable physical storage device being configured to transfer the digital prescription file to the remote medical device in the patient's home for use in conducting the medical procedure.

18. The system of claim 1, wherein:

the prescription parameters comprise treatment parameters for use in conducting a medical treatment on the patient using the remote medical device; and performing the compatibility check further comprises:

performing a calculation based on the treatment parameters to determine at least one characteristic of the medical treatment; and comparing a result of the calculation to the operational parameters of the remote medical device from the database.

19. The system of claim 18, wherein:

the operational parameters of the remote medical device includes capacity limits;

performing the calculation based on the treatment parameters comprises determining a total fluid delivery of the medical treatment; and comparing the prescription parameters to the operational parameters of the remote medical device further comprises comparing the total fluid delivery to the capacity limits of the remote medical device.

20. The system of claim 1, where the clinical information system comprises:

a healthcare computer network that is independent from the computer server, the healthcare computer network comprising:

at least one server configured to maintain and store patient health records, and a plurality of user terminals configured to provide point-of-care access to the patient health records by medical professionals.

21. The system of claim 1, wherein the network is the Internet.

* * * * *